United States Patent [19]
Fujieda et al.

[11] Patent Number: 5,764,341
[45] Date of Patent: Jun. 9, 1998

[54] OPHTHALMIC APPARATUS

[75] Inventors: Masanao Fujieda, Toyohashi; Naoki Isogai, Nishio, both of Japan

[73] Assignee: Nidek Co., Ltd., Aichi, Japan

[21] Appl. No.: 754,933

[22] Filed: Nov. 25, 1996

[30] Foreign Application Priority Data

Nov. 30, 1995 [JP] Japan .................................. 7-337911

[51] Int. Cl.$^6$ .................................................. A61B 3/10
[52] U.S. Cl. ............................................ 351/221; 351/205
[58] Field of Search ................................... 351/221, 205, 351/211, 210, 209, 206, 208, 200, 246

[56] References Cited

U.S. PATENT DOCUMENTS 5,406,076  4/1995  Mimura et al. .
5,502,519  3/1996  Hosoi .
5,532,769  7/1996  Miwa et al. .

*Primary Examiner*—Hung X. Dang
*Attorney, Agent, or Firm*—Oliff & Berridge, PLC

[57] ABSTRACT

An ophthalmic apparatus in which a measuring part for inspecting-or-measuring an eye to be examined is disposed so as to move relatively against a fixation stand, the ophthalmic apparatus comprises light source for use in detecting a relative movement, which is disposed in the one between the fixation stand side and the measuring part side, photo detecting elements for detecting a light bundle emitted from the light source for use in detecting a relative movement, which is disposed in the other between the fixation stand side and the measuring part side, target forming device for forming at least two target-images, that are transmitted from the light source for use in detecting a relative movement onto the photo detecting elements plane, upon before and after the movement according to the relative movement by the measuring device against the fixation stand, and calculating device for calculating a relative position of the measuring part against the fixation stand based on a detecting information of the target images detected by the photo detecting elements.

17 Claims, 9 Drawing Sheets

5,764,341

1

OPHTHALMIC APPARATUS

BACKGROUND OF THE INVENTION

1. Field of the Invention

The present invention relates to an ophthalmic apparatus for inspecting or measuring an eye to be examined, and more particularly, it relates to a mechanism suitable for detecting a relative position of a measuring part contained in the ophthalmic apparatus which moves the measuring part for inspecting or measuring the eye to be examined relatively against a fixation stand.

2. Description of Related Art

As an ophthalmic apparatus such as an objective eye-refractive power measuring apparatus and the like, a lot of fixed-types are known. Concerning this apparatus of a fixed-type, in general, an inspecting-measuring part is constructed so as to move relatively against a fixation stand, and an alignment is performed by moving the inspecting-measuring part against an eye to be examined, after that inspection or measurement are performed. Therefore, referring to such an ophthalmic apparatus, an interpupilary distance of an examinee can be known by obtaining quantities of movement in a right and left direction by the inspecting-measuring part upon aligning the one eye based on a state of another eye which has been aligned.

As a moving distance detecting mechanism for obtaining a moving distance of the inspecting-measuring part, such one as shown in FIG. 9 is known. A movable part 101 having an inspecting-measuring part 100 moves to a right and left direction against a fixation stand 102 by operating a joystick or the like. Two pulleys 103s are installed in the fixation stand 102 side, and a wire 104 is laid across both pulleys 103s, and this wire is fixed to a block 101a which is one part of the movable part 101. Further, the wire 104 is wound around a pulley of a potentiometer 105. The movable part 101 moves to a right and left direction, by which the potentiometer 105 rotates through the wire 104, and quantity of movement in a right and left direction is detected based on its rotating quantity.

Referring to such a mechanism for detecting a moving distance as described above, a distance can be comparatively and easily detected well-sufficiently and accurately. However, in the case that the measuring-part section is constructed so as to be capable of moving to a right and left direction relatively against the movable part in order to make an alignment relative to the examined eye automatic, two sets are needed in such a detecting mechanism that mentioned above, therefore it results in such a problem that structure of an apparatus comes to be complicated. Also, to contain two sets of the detecting mechanisms has no utility in the economical point of view.

SUMMARY OF THE INVENTION

The present invention has been made in view of the above circumstances and has an object to overcome the above problems and to provide an ophthalmic apparatus, which has such simple construction that has only one set of a mechanism for detecting a relative movement, and can easily detect a relative position in a movable-part side (for example, a measuring part) which is capable of moving relatively against a fixation part (for example, a fixation stand) of the apparatus.

Additional objects and advantages of the invention will be set forth in part in the description which follows and in part will be obvious from the description, or may be learned by

2 practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus of the present invention in which a measuring part for inspecting-or-measuring an eye to be examined is disposed so as to move relatively against a fixation stand, the ophthalmic apparatus comprises light source for use in detecting a relative movement, which is disposed in the one between the fixation stand side and the measuring part side, photo detecting elements for detecting a light bundle emitted from the light source for use in detecting a relative movement, which is disposed in the other between the fixation stand side and the measuring part side, target forming means for forming at least two target-images, that are transmitted from the light source for use in detecting a relative movement onto the photo detecting elements plane, upon before and after the movement according to the relative movement by the measuring means against the fixation stand, and calculating means for calculating a relative position of the measuring part against the fixation stand based on a detecting information of the target images detected by the photo detecting elements.

The ophthalmic apparatus of the present invention comprises movable part for moving relatively against a fixation stand by an examinee's operation, and measuring-part-moving-means for moving further a measuring part relatively against the movable part.

The ophthalmic apparatus in another aspect of the present invention in which a measuring part for inspecting-or-measuring an eye to be examined is disposed so as to move relatively against a fixation stand, the ophthalmic apparatus comprises light source for use in detecting a relative movement, which is disposed in the one between the fixation stand side and the measuring part side, photo detecting elements for detecting a light bundle emitted from the light source for use in detecting a relative movement, which is disposed in the other between the fixation stand side and the measuring part side, target forming means for forming at least two target-images, that are transmitted from the light source for use in detecting a relative movement onto the photo detecting elements plane, upon before and after the movement according to the relative movement by the measuring means against the fixation stand, vertical position detecting means for detecting a position in a vertical direction of the measuring part against the fixation stand, and calculating means for calculating a relative position in a before-and-behind direction of the measuring part against the fixation stand based on a detecting information detected by the vertical position detecting means and the photo detecting elements.

According to the present invention, a relative position of a movable part side capable of moving relatively against a fixation part is obtained easily with a simple construction. Further, in the case that a second movable part is further arranged on the movable part, a relative position against a fixation part of this second movable part is also obtained easily.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.
[General Construction]

Figure 1:
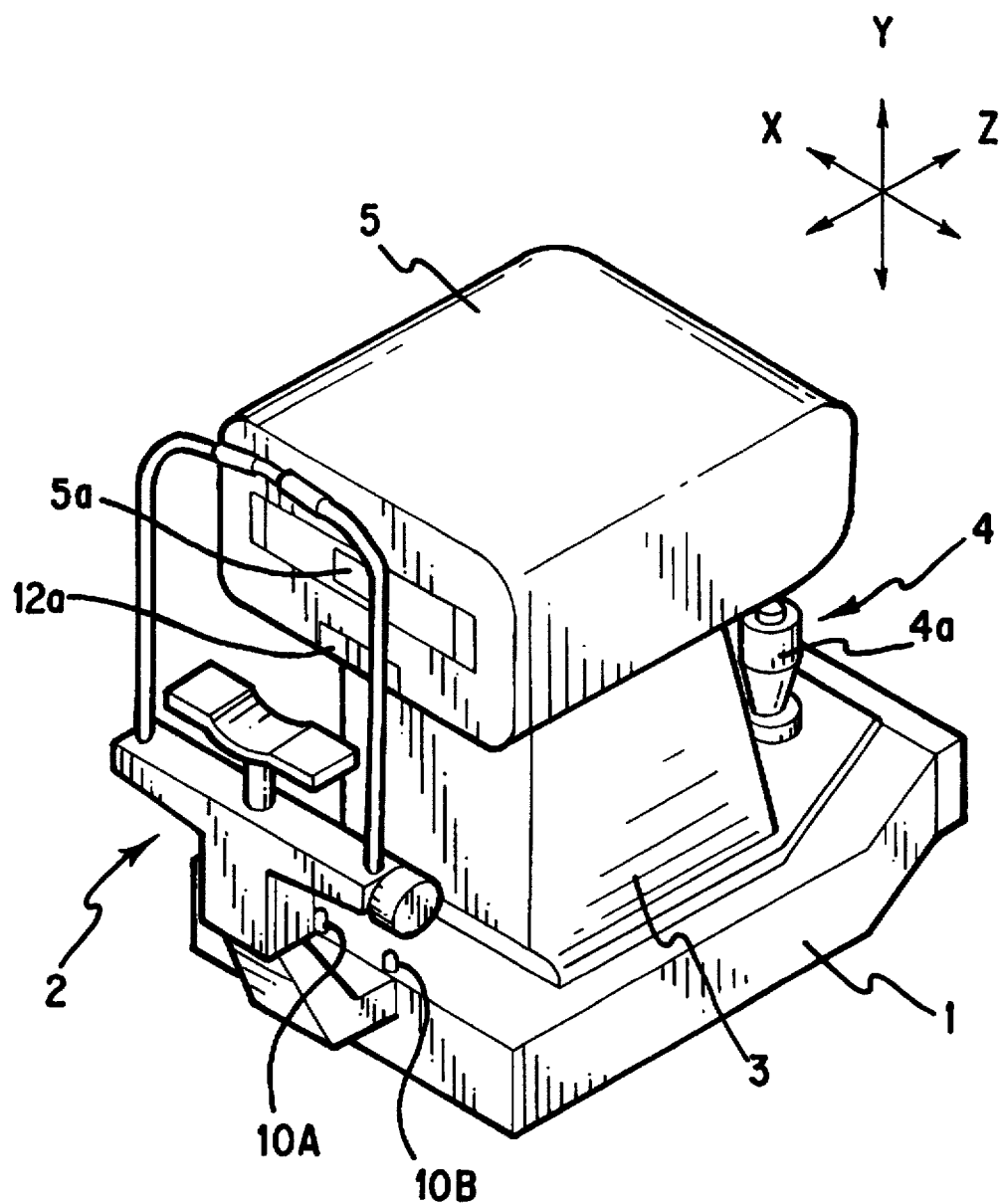
FIG. 1 is an outer perspective view of an automatic eye-refractive power measuring apparatus according to the preferred embodiment.

FIG. 1 is an outer perspective view of an automatic eye-refractive power measuring apparatus according to the preferred embodiment. Reference numeral 1 is a fixation stand, to which a head holding part 2 for fixing an examinee's head part is fixed. Additionally, light sources 10A and 10B included in a system for detecting a position of a measuring part, mentioned below, are disposed in the examinee's side on the fixation stand 1. Reference numeral 3 is a movable part of the apparatus for sliding-and-moving in a before and behind (Z) direction and a right and left direction (X) against the fixation stand 1 by operating a joystick 4 manually. In the examiner's side of the movable part 3 of the apparatus, a monitor for observing an eye to be examined and some kinds of switches are arranged. Both a movement and a slight movement in a before and behind direction and a right and left direction by the movable part 3 of the apparatus are actualized by a construction of a spherical part 6a and a lower-end part 6b that are formed on a downward position to an axis disposed inside of the joystick 4, a sliding plate 6c to which the lower-end part 6b shakes and moves, a friction plate 6d appended on the fixation stand 1 contact with the sliding plate 6c and a spherical bearing 6e disposed inside of a housing 3a which is in a body with the movable part 3 of the apparatus (see FIG. 2).

Figure 2:
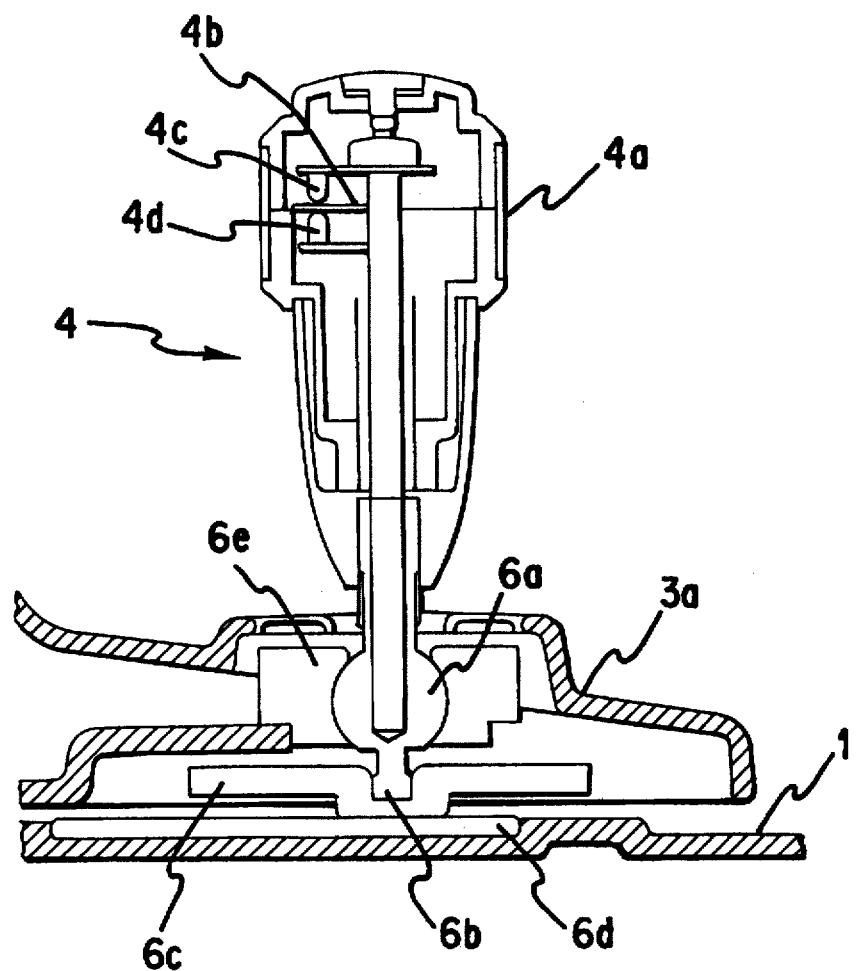
FIG. 2 is an view showing a mechanism for a joystick.

Reference numeral 5 is a measuring part, in which an alignment/observation optical system, a refractive power measuring optical system and a photo-receiving part in below-mentioned system for detecting a position of a measuring part or the like are held, and a measuring-window 5a for being passed through by a measuring light bundle and the like is disposed at approximate center in a right and left direction, where is opposite side to the examiner being close to at the measuring part 5. Concerning the measuring part 5, if a rotation lever 4a provided with the joystick 4 is operated so as to rotate, then a Y-direction (upper and lower) driving device goes into run, and thereby the measuring part 5 moves in an upper and lower direction against the movable part 3 of the apparatus. This upper and lower movement is performed by driving-and-controlling a motor contained in the Y-direction driving device based on the detected result which is obtained on the basis of a rotation direction and a rotation quantity of the rotation lever 4a based on a signal transmitted from the photo detecting element 4d by means of a slit plate 4b which rotates together with the rotation lever 4a, a light source 4c and a photo detecting element 4d that are arranged at an axis so as to put the slit plate 4b therebetween, as shown in FIG. 2. A detailed description for these mechanisms concerning the joystick is disclosed in Japanese Patent Publication No.HEI6(1994)-7292 (corresponding to U.S. Pat. No. 5,406,076) by the applicant of the present invention, so it is wanted to be referred.

Further the measuring part 5 moves in a right and left direction and an upper and lower direction against the movable part 3 of the apparatus by making each motor of the X-direction (right and left) driving apparatus and the Y-direction (upper and lower) direction driving apparatus go into run in order to carry out an automatic alignment based on the detected result of an alignment condition detected by below-mentioned alignment optical system.
[Construction for respective parts]

Next, construction for respective important parts of this apparatus will be described hereinafter by dividing them into a position detecting system of measuring part, an alignment/observation optical system, and a controlling system. Still, an automatic eye-refractive power measuring apparatus measures a refractive power based on projecting a target onto a fundus of an eye to be examined and then detecting a reflecting-target image transmitted from the fundus of the eye by using a photo receiving means, however this measuring mechanism of itself has little relationship to the present invention, and a well-known art can be used instead of the mechanism, therefore the description is omitted.
<Position detecting system of measuring part>

Figure 3B:
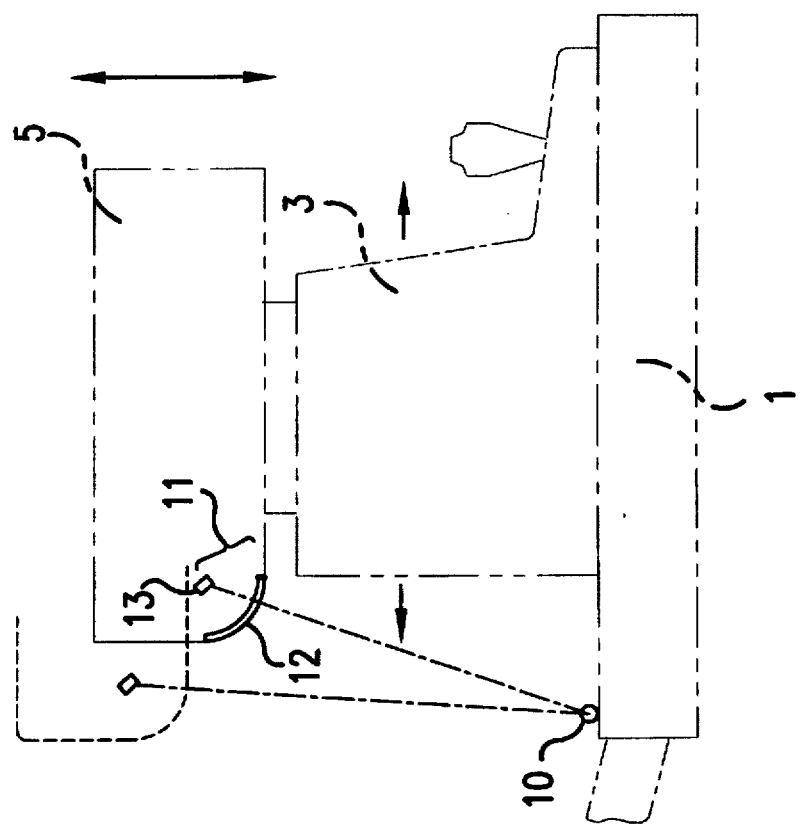
FIGS. 3(a) and 3(b) are views for illustrating a position detecting system for detecting a relative position in a right and left direction of a measuring part against a fixation stand.
Figure 3A:
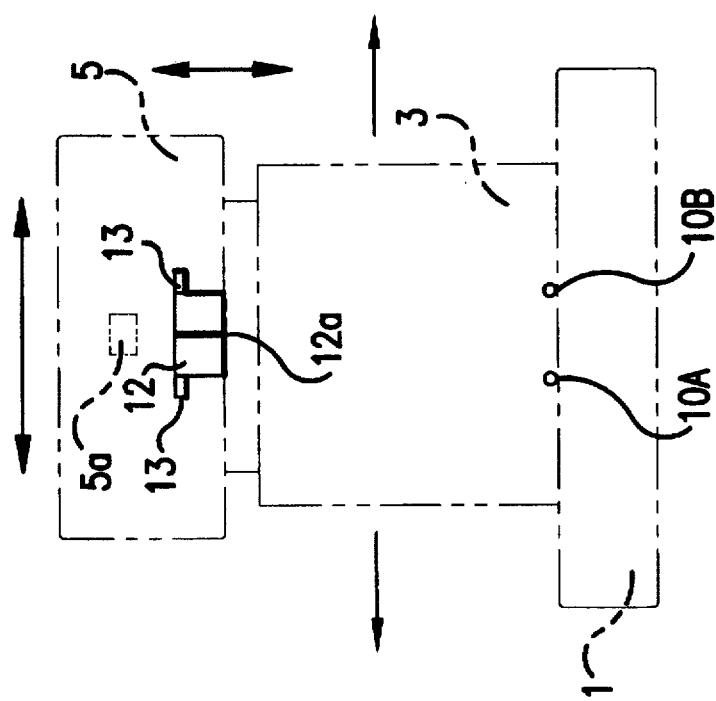

FIGS. 3(a) and 3(b) are views for illustrating a position detecting system for detecting a relative position in a right and left direction of the measuring part 5 against the fixation stand 1. Reference numeral 10A and 10B are light sources such as a LED or the like, for use in detecting a position, which generate lights within a range of infrared-rays, and two pieces (10A and 10B) are disposed close to the examiner being at the fixation stand 1 at intervals of a predetermined distance with defining a middle of a right and left direction as a center. As the light sources 10A and 10B for use in detecting, the light sources of which emission angles are comparatively large are used, and thereby, even if the measuring part 5 moves to both movable limits in a right and left direction relatively against the fixation stand 1, a detected light is transmitted to the light receiving part 11 arranged in the measuring part 5 side.

The light receiving part 11 is consisted of a slit 12 and an one-dimensional photo detecting element 13. The slit 12 has one piece of a slit aperture 12a extending in a longitudinal direction, and as shown in FIG. 3(b), it has an arc shaped line from a side view. The slit aperture 12a is disposed at an approximate center in a right and left direction of the measuring part 5, and the one-dimensional photo detecting element 13 having a detecting-plane along with a right and left direction is disposed at an approximate center of curvature of its arc. As the one-dimensional photo detecting element 13, the detecting elements such as a CCD, a PSD and the like can be used.

Lights emitted from two pieces of light sources 10A and 10B illuminate the slit 12. Each of light bundles limited by the slit aperture 12a reaches to the one-dimensional photo detecting element 13, and the one-dimensional photo detecting element 13 detects a relative position of the measuring part 5 in a right and left direction against the fixation stand 1 according to the positions of two pieces of slit images.

Figure 4:
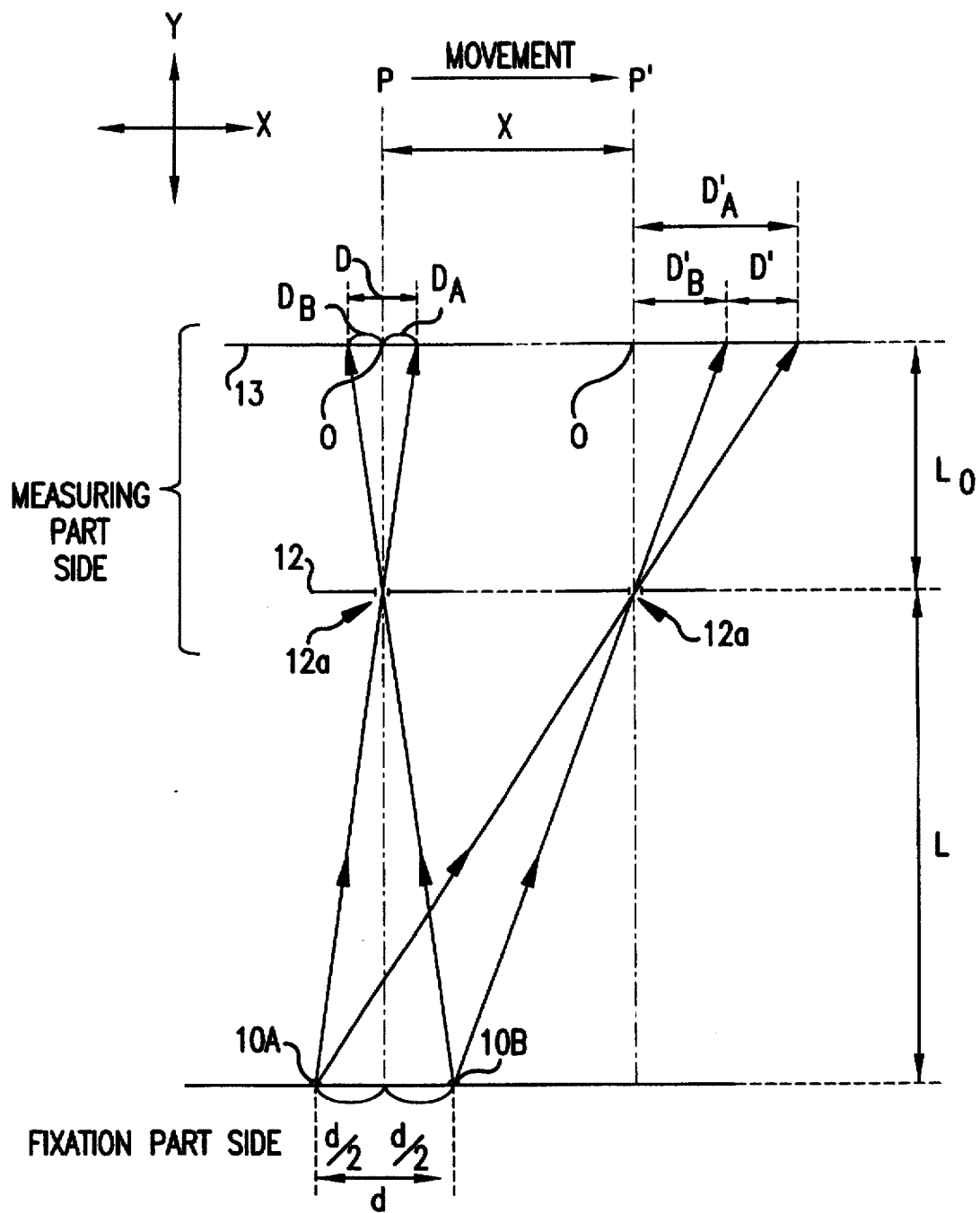
FIG. 4 is a view for illustrating a method for detecting a relative position in a right and left direction of a measuring part.

This method for detecting a relative position will be described referring to FIG. 4 (in following, before and behind (Z) direction is defined as constant and a X-Y plane is taken into consideration to make a description easier).

First of all, a distance detection in a Y-direction of the measuring part 5 from the fixation stand 1 is taken into consideration. Here, a perpendicular-plane at midpoint of light sources 10A and 10B disposed at intervals of a predetermined distance d is defined as a standard position P, and the slit aperture 12a of the light receiving part 11 is defined as that it is at a position P' only a x-distance apart in a right and left (X) direction, and in a vertical direction (Y), it is defined as that the slit aperture 12a is at a L-distance apart in a vertical direction from an axis line of two pieces of the light sources 10A and 10B. Also, a distance is defined as $L_o$ (a predetermined distance) from the slit aperture 12a to a detecting plane of the one-dimensional photo detecting element 13. Then, if the interval between the slits on the one-dimensional photo detecting element 13 caused by the two pieces of light sources 10A and 10B is defined as D', there is a relationship given by the following expression:

$$D':d=L_o:L \qquad (1)$$

(an interval D between the slit images caused by two pieces of light sources 10A and 10B at a right and left standard position P is also the same as this, and it means that, in the case that L is constant, the interval between the slit-images is unchanged even if the measuring part 5 moves in a right and left direction). According to this relationship, a distance L is given by the following expression:

$$L=(d/D') * L_o \qquad (2)$$

Where, $L_o$ and d are defined under a design, therefore the distance L is decided by detecting the interval D' between the slit images on the one-dimensional photo detecting element 13 and by calculating (in consideration of a before and behind (Z) direction, L is a distance on a Y-Z plane).

If a distance L can be decided, a moving distance x of a position P' in a right and left direction against a standard position P in a right and left direction is obtained by detecting a displacement of the slit-image on the one-dimensional photo detecting element 13, which is formed by at least either the light source 10A or the light source 10B. For example, a point O on the one-dimensional photo detecting element 13 placed at right above of the slit aperture 12a is defined as a standard point (in figure, a right direction is defined as "+" and a left direction is defined as "−" against the standard point O). In consideration of the slit image caused by the light source 10A, if a quantity of a displacement from the standard point O to the slit image upon placing at a position P' is defined as $D'_A$, referring to the figure, there is a relationship given by the following expression:

$$D'_A : (x+d/2)=L_o:L \qquad (3)$$

Therefore a moving distance x in a right and left direction is given by the following expression:

$$x=(L/L_o) * D'_A-(d/2) \qquad (4)$$

Then if L of the expression (2) is substituted for the expression (4), the following expression is given:

$$x=(D'_A/D') * d-(d/2) \qquad (5)$$

Additionally, in consideration of the slit image caused by the light source 10B, if a quantity of a displacement from a standard point O to the slit image is defined as $D'_B$, a moving distance x in a right and left direction is given by the following expression, same as the method for finding by using the light source 10A:

$$x=(D'_B/D') * d+(d/2) \qquad (6)$$

In these expressions (5) and (6), since d is a value known in advance, which is decided under a design, therefore a moving distance x of a position P' in a right and left direction against a standard position P in a right and left direction can be obtained by detecting an interval D' of a slit image and a quantity $D'_A$ of a displacement of a slit image caused by the light source 10A (or a quantity $D'_B$ of a displacement of a slit image caused by the light source 10B) and by calculating them (preferably, it is desirable to find an average of the distances based on the quantities $D'_A$ and $D'_B$ of displacements of respective slit images).

Additionally, whether the measuring part 5 is in a right direction or in a left direction against a middle point of a right and left direction of the fixation stand 1 (or, whether a measuring eye is a right eye or a left eye) can be obtained easily by detecting that whether a middle of the two slit images on the one-dimensional photo detecting element 13 is in either direction against a detecting standard point O.

Still, a detection of a relative position in a right and left direction is a method for finding it by desiring a standard position O for detecting on the one-dimensional photo detecting element 13 in advance, however, it is considered that when the measuring part 5 is placed at a certain relative position against the fixation stand 1, a position of a slit image on the one-dimensional photo detecting element 13 can be defined as a detecting standard.

Also, above-mentioned position detecting system, the two pieces of light sources 10A and 10B are arranged, however a greater number of pieces can be allowed, and an arrangement of the fixation stand 1 and the measuring part 5 for light sources 10A and 10B and the light receiving part 11 (the slit 12 and the one-dimensional photo detecting element 13) can be reversed.

<Alignment/observation optical system>

Figure 5:
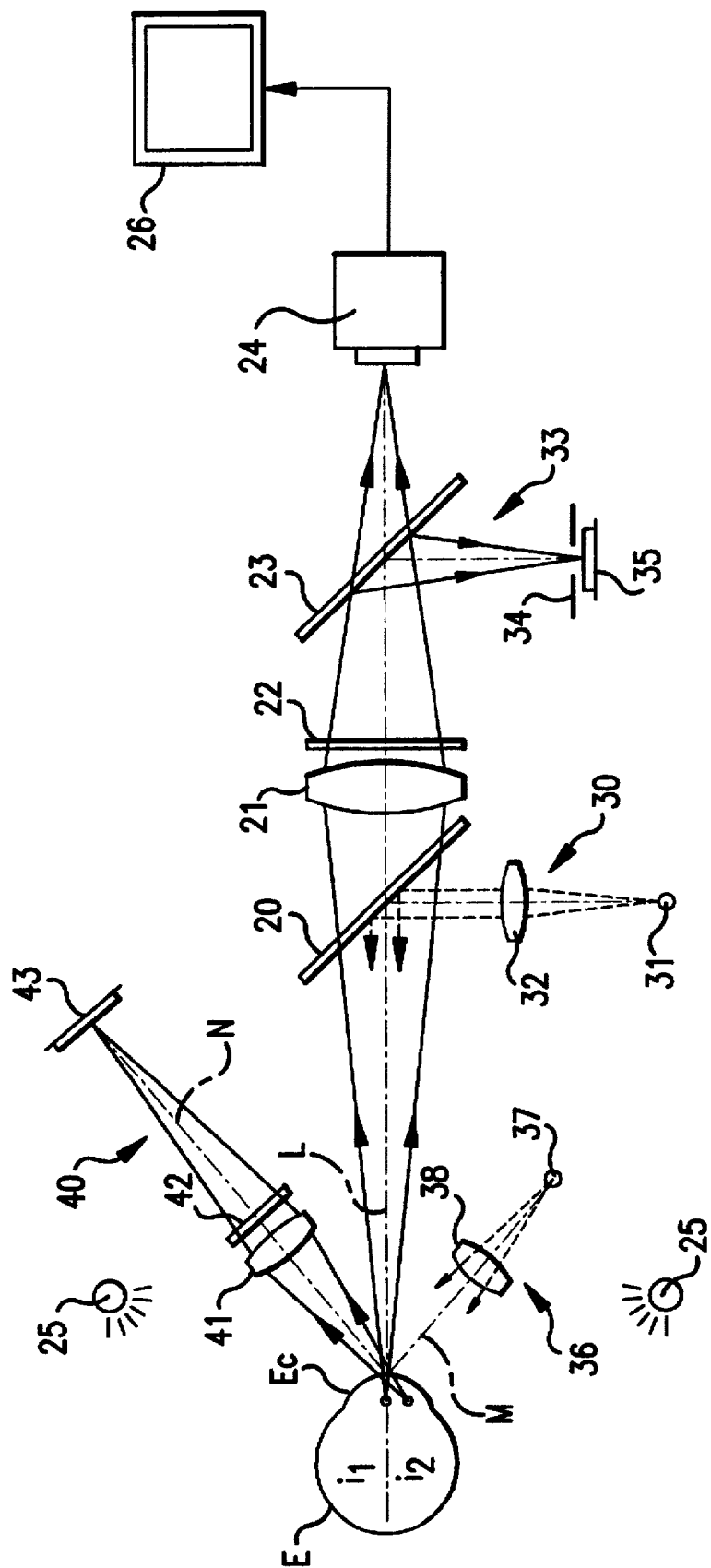
FIG. 5 is a view showing an alignment/observation optical system disposed in a measuring part.

FIG. 5 is a view showing an alignment/observation optical system disposed in the measuring part 5. On an optical axis L in the observation optical system, from the eye to be examined, a half mirror 20, an objective lens 21, filter 22, a half mirror 23 and a TV camera 24 are disposed. The filter 22 transmits through a wavelength of a light bundle of below-mentioned front target projecting optical system and cuts a wavelength of a light bundle in a distance target projecting optical system. Reference numeral 25 is an illuminating light source of an anterior portion of an eye for generating a light within a range of infrared-rays. An image of an anterior portion of the eye which is illuminated by the illuminating light source 25 is focused on the focusing plane of the TV camera 24, and then it is projected onto a TV monitor 26.

Reference numeral 30 is a front target projecting optical system. Light within a range of near infrared-rays which is emitted from a light source 31 is made to be a parallel light bundle by a projection lens 32, and then is reflected by the half mirror 20 and irradiated to a cornea of the eye to be examined. This light bundle is mirrored-and-reflected by the cornea, and then forms a target $i_1$, which is a virtual image of the light source 31, onto the eye E to be examined. A light bundle of the target $i_1$ forms an image of the target $i_1$ onto the focusing plane of the TV camera 24 by means of an observation optical system.

Reference numeral 33 is a front target detecting optical system. A light bundle of the target $i_1$ which is formed by a mirror-reflection of the cornea is reflected by the half mirror 23, and is led to the front target detecting optical system 33, and then passes through a field stop 34, then is received by a two-dimensional CCD 35. On the basis of a position of the target image which is received, the two-dimensional CCD 35 detects a position of the eye to be examined of an upper and lower direction and a right and left direction against an observation optical axis L (a measuring optical axis).

Reference numeral 36 is a distance target projecting optical system, in which a projecting optical axis M is arranged so as to incline to the observation optical axis L, and both of optical axes are intersecting at the position at interval of the predetermined working distance. On the optical axis M, a light source 37 (which emits a light of which a wavelength is different from the front target projecting light source 31) and a projection lens 38 is disposed, and a light emitted from the light source 37 is made to be a parallel light bundle by the projection lens 38 and then is irradiated to the cornea of the eye to be examined. A light bundle mirrored-and-reflected by the cornea forms a target $i_2$ which is a virtual image of the light source 37.

Reference numeral 40 is a distance target detecting optical system, and N is an optical axis. The optical axis N and the optical axis M are symmetry about the optical axis L, and the optical axis N and the optical axis M intersect at the optical axis L. On the optical axis N, a photo receiving lens 41, a filter 42 and an one-dimensional CCD 43 are disposed. The filter 42 transmits through a light having a wavelength of the light source 37, and it has no characteristic that it transmits through a light having a wavelength both of the illumination light source 25 and the light source 31. A light bundle of the target $i_2$ which is reflected by the cornea of the eye to be examined transmits into the one-dimensional CCD 43 through the filter 42 by means of the photo receiving lens 41. If the eye to be examined moves to a direction of the optical axis L (a before and behind direction), an image of the target $i_2$ caused by the photo receiving lens 41 also moves to a detecting direction of the one-dimensional CCD 43. The one-dimensional CCD 43 detects a position of the eye to be examined in a before and behind direction against an approximate work distance based on this position of the target image.

<Control system>

Figure 6:
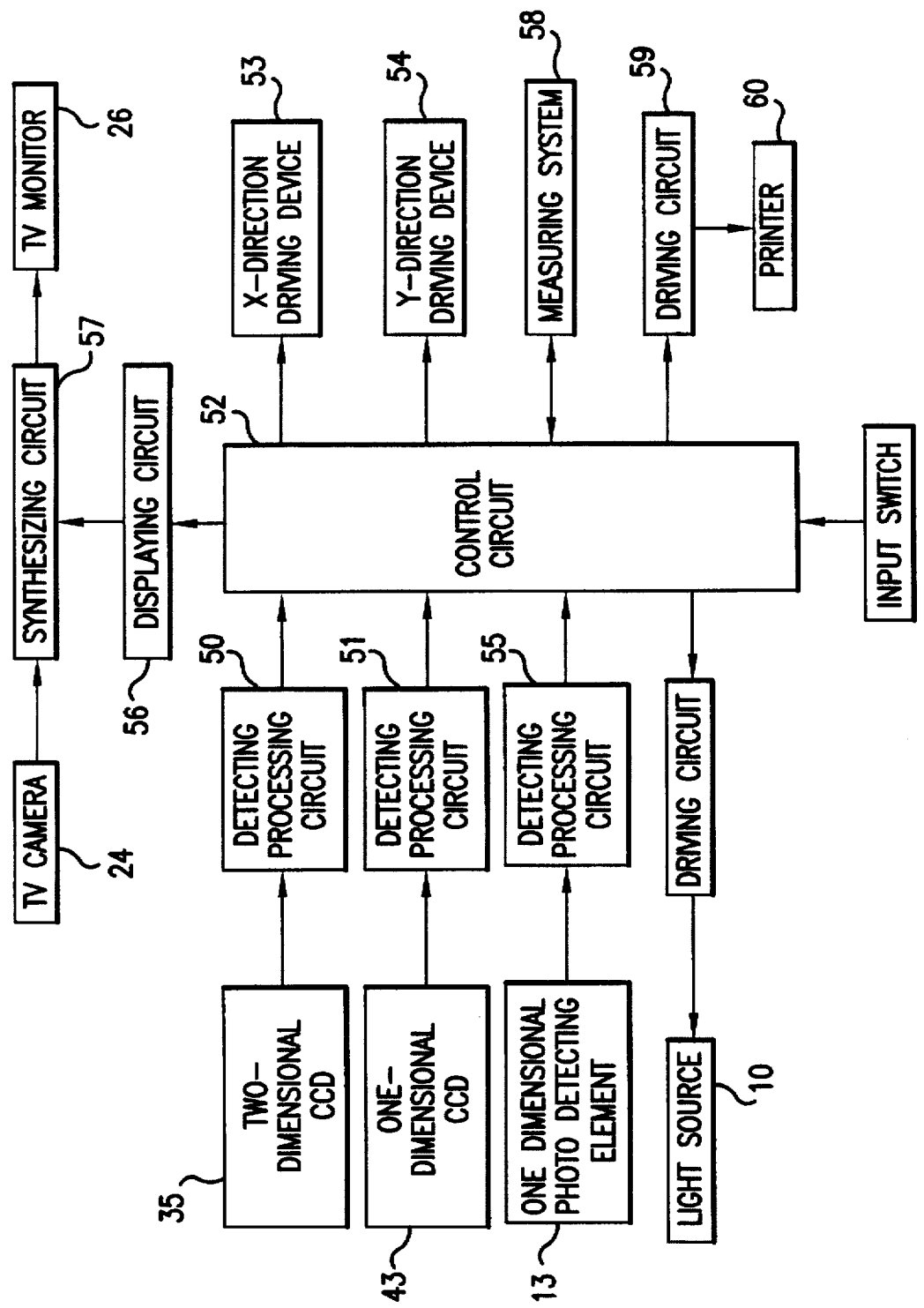
FIG. 6 is a block diagram for a control system of an important part of an apparatus.

FIG. 6 is a block diagram for a control system of an important part of the apparatus. Each signal transmitted from the CCDs 35 and 43 in the alignment optical system is inputted to a control circuit 52 through detecting-processing circuits 50 and 51. The control circuit 52 obtains a quantity of a displacement against an approximate position of the eye E to be examined in an upper and lower direction, a right and left direction and a before and behind direction based on the inputted signal.

Reference numeral 53 is a X-direction driving device for moving the measuring part 5 in a right and left direction against the movable part 3 of the apparatus, and reference numeral 54 is a Y-direction driving device for moving the measuring part 5 in a upper and lower direction . These driving devices are consisted of a motor, a motor driving circuit and the like, and drive them respectively based on information of a displacement obtained by the control circuit 52 based on detecting signals of the CCDs 35 and 43, and thereby these driving devices work as an automatic alignment. Still, in the preferred embodiment, a driving device for making the measuring part 5 move in a before and behind (Z) direction against the movable part 3 of the apparatus is not installed, however it may be installed by making use of a signal transmitted from the one-dimensional CCD 43.

Also, an output signal transmitted from the one-dimensional photo detecting element 13 in a measuring part position detecting system is processed by a predetermined procedure by a detecting-processing circuit 55 and then inputted to the control circuit 52, then the control circuit 52 executes above-mentioned arithmetic process, and thereby a quantity of a displacement in a right and left direction of the measuring part 5 is obtained.

Reference numeral 56 is a displaying circuit for generating figures, characters and the like on the TV monitor 26, that are used for informing of some kinds of information, and reference numeral 57 is a synthesizing circuit for synthesizing a displaying information generated by the displaying circuit 56 with an image-signal transmitted from the TV camera 24.

The operation of the apparatus having such architecture as described above will be described hereinafter. Concerning the apparatus, either a manual alignment or an automatic alignment can be selected by using a mode changing-over switch, however the case that the automatic alignment is selected will be described here.

If a power source of the apparatus is turned on and then the automatic alignment is selected, the control circuit 52 makes the X-direction driving apparatus go into run and makes the measuring part 5 so as to be placed at a standard position (a middle position of a movable range) against the movable part 3 of the apparatus.

Next, the examiner fixes the head of the examinee to the head holding part 2, after that the examiner operates the joystick 4, and moves horizontally the movable part 3 of the apparatus in a before and behind direction and a right and left direction against the fixation stand 1, and at first, an alignment for the one eye in the measuring eye side is performed. At the time, the control circuit 52 processes a detecting signal transmitted from above-mentioned one-dimensional photo detecting element 13, and thereby the control circuit 52 obtains a moving direction of the measuring part 5 in a right and left direction and a moving quantity against a middle position of a right and left direction of the fixation stand 1 at any time, and then judges whether the measuring eye is a right side or a left side according to the moving direction.

Concerning an alignment of the measuring eye in a right and left direction and an upper and lower direction, if the examiner aligns by operating the joystick 4 and the rotation lever 4a with his eye observing the image of the anterior portion of the eye which is projected onto the TV monitor 26 and a reticle for aiming (not shown), the target image comes to be detected by the two-dimensional CCD 35, therefore the control circuit 52 performs an automatic alignment by making the X-direction driving device 53 and the Y-direction driving device 54 go into run.

Concerning an alignment in a before and behind direction, it is performed by moving the movable part 3 of the apparatus to a before and behind direction by means of an operation of the joystick 4 in response to a distance mark display (not shown) which is generated by the displaying circuit 56 based on a quantity of a displacement, obtained by the control circuit 52 by means of the one-dimensional CCD 43, and then is displayed at the TV monitor 26.

Respective target images in the alignment optical system move on the two-dimensional CCD 35 and the one-dimensional CCD 43 by works performed by respective driving devices and an alignment by the examiner. The control circuit 52 judges whether an alignment condition detected on the basis of a position of this target image is in the predetermined permissible limit or not, and whether it satisfies the predetermined condition for starting the measurement or not. If the predetermined condition for the measurement is satisfied, the control circuit 52 controls respective driving devices so that they may be stopped, and thereby it completes the alignment. The control circuit 52 generates a trigger signal automatically and makes a measuring system 58 go into run, then executes the measurement. The obtained-result of the measurement is displayed at the TV monitor 26 and is stored in a memory circuit in the control circuit 52. Also, when an alignment has been completed, the control circuit 52 obtains a moving quantity (an interpupilary distance of one eye) against a standard position of the measuring part 5 (at the center in the right and left direction of the fixation stand 1), which is found by performing above-mentioned calculating process, based on a signal transmitted from the one-dimensional photo detecting element 13 in the measuring part position detecting system, and then the control circuit 52 stores the moving distance in the memory circuit.

After a measurement for the one eye has been completed, the other eye is measured. If the measuring part 5 together with the movable part 3 of the apparatus made to move to the side of the other eye by operating the joystick 4, a slit image on the one-dimensional photo detecting element 13 moves, therefore the control circuit judges whether a measuring eye is changed-over or not, and then it changes-over a measuring mode of right and left eye. As the same way described above, if the manual alignment and the automatic alignment by each driving device have been completed and the measurement has executed, the control circuit 52 performs an arithmetic process based on a position of a slit image on the one-dimensional photo detecting element 13, and thereby the control circuit 52 obtains a moving quantity of the measuring part 5 in a right and left direction against a standard position of the other eye and then stores it therein.

The measurement for both eyes has been finished as described above, the control circuit 52 obtains an interpupilary distance based on each moving quantity (an interpupilary distance of one eye) of the measuring part 5 (it is also considered that it can be obtained on the basis of a moving quantity of the measuring part 5, upon moving from completion of an alignment for one eye to completion of an alignment for the other eye). The obtained-result is printed out from a printer 60 through a printer driving circuit 59.

As described above, the description has been performed by making a detection of a relative position in a right and left direction against the fixation stand 1 of the measuring part 5 as an aspect, however a relative position in a before and behind direction can be also obtained by making use of information of a detection by the measuring part position detecting system which is mentioned above.

Figure 7:
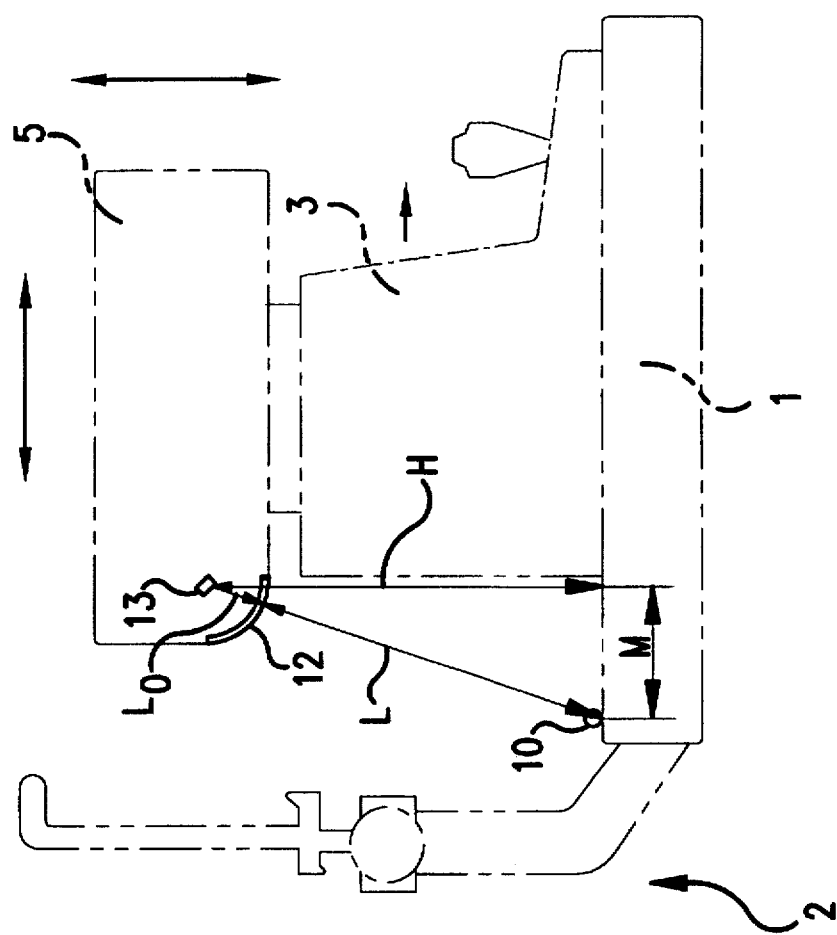
FIG. 7 is a view for illustrating a method for obtaining a relative position in a before and behind direction of a measuring part.

The method for obtaining a relative position in a before and behind direction is will be described referring to FIG. 7. In the figure, L and Lo are defined as the same as described in FIG. 4. If H is defined as a distance in a vertical direction from an upper plane of the fixation stand 1 to a detecting plane of the one-dimensional photo detecting element 13, and M is defined as a distance in a before and behind direction from the light source 10 to a detecting plane of the one-dimensional photo detecting element 13, a distance M is given by the following expression:

$$M=[(L+L_o)^2-H^2]^{1/2} \qquad (7)$$

Where, $L_o$ is known in advance since it is defined under a design, and L as described in the expression (2) is decided by detecting an interval between the slit-images on the one-dimensional photo detecting element 13 and by calculating. H is found according to a revolution per minute of a motor moving to an upper and lower direction in the measuring part 5 (in the case of a pulse motor, a number of pulses to be driven) or an installation of a potentiometer installed specially as a well-known distance detecting means. Therefore a distance M in a before and behind direction can be obtained by substituting these values for the expression (7) and by calculating.

As is described above, if a distance in before and behind direction of the measuring part 5 against the fixation stand 1 can be obtained, in the case of an ophthalmic apparatus of which a working distance between an eye to be examined and the apparatus is particularly short, it is utilized for ensuring its safety distance. As an apparatus of which a working distance is particular short with an eye to be examined, for example, a non-contact tonometer (eye pressure gauge), a fundus camera, corneal topography having a small placido ring and the like are known. In general, an ophthalmic apparatus usually has a peculiar working distance of the apparatus itself, therefore in consideration of this working distance and a distance M in a before and behind direction which is found as described above, a safety distance between the measuring part 5 which moves to a before and behind direction and the eye to be examined is desired. A distance M is detected at any time, if the measuring part 5 is close to the eye to be examined with exceeding a permissible range of a safety distance, it is informed the examiner by displaying a warning about it or sounding something. Or, a safety mechanism such as a brake and the like is made to go into run based on information of a distance M.

Further, in the case that the measuring part 5 is made to move also in a before and behind direction against the movable part 3 of the apparatus by means of a before and behind direction driving device such as a motor in order to perform an automatic alignment, the measuring part 5 can be driven according to information of a position in a before and behind direction mentioned above, therefore it is particularly convenient. The measuring part 5 is made to go into run as following. Upon starting after the power source is turned on, the measuring part 5 is made to move to a safety region where is sufficiently apart from the eye to be examined. Upon measuring, on the basis of information of a working distance caused by an alignment optical system, the measuring part 5 is made to drive and bring into closer to the eye. When it comes to be the predetermined alignment condition, the measuring part 5 is stopped being driven, and a measurement is started. After the measurement has finished, the measuring part 5 is made so as to move to a well-safety region over again.

As is described above, without complicating an apparatus, a position in a before and behind direction can be found. Particularly, concerning a movement of the measuring part in a before and behind direction caused by the automatic alignment mechanism, it can be easily to ensure a safety distance between the examiner and the apparatus, therefore the operation performance is improved better.

[The second embodiment]

In the first preferred embodiment, a relative position of the measuring part 5 in a before and behind direction against the fixation stand 1 is detected by using two pieces of light sources and one slit aperture, on the contrary, in the second preferred embodiment, it is detected by using one piece of light source and two pieces of slit apertures (description for construction of respective parts is omitted since it is basically the same as the first preferred embodiment with the exception of that a number of light sources and a number of slit apertures are different from the first embodiment).

Figure 8:
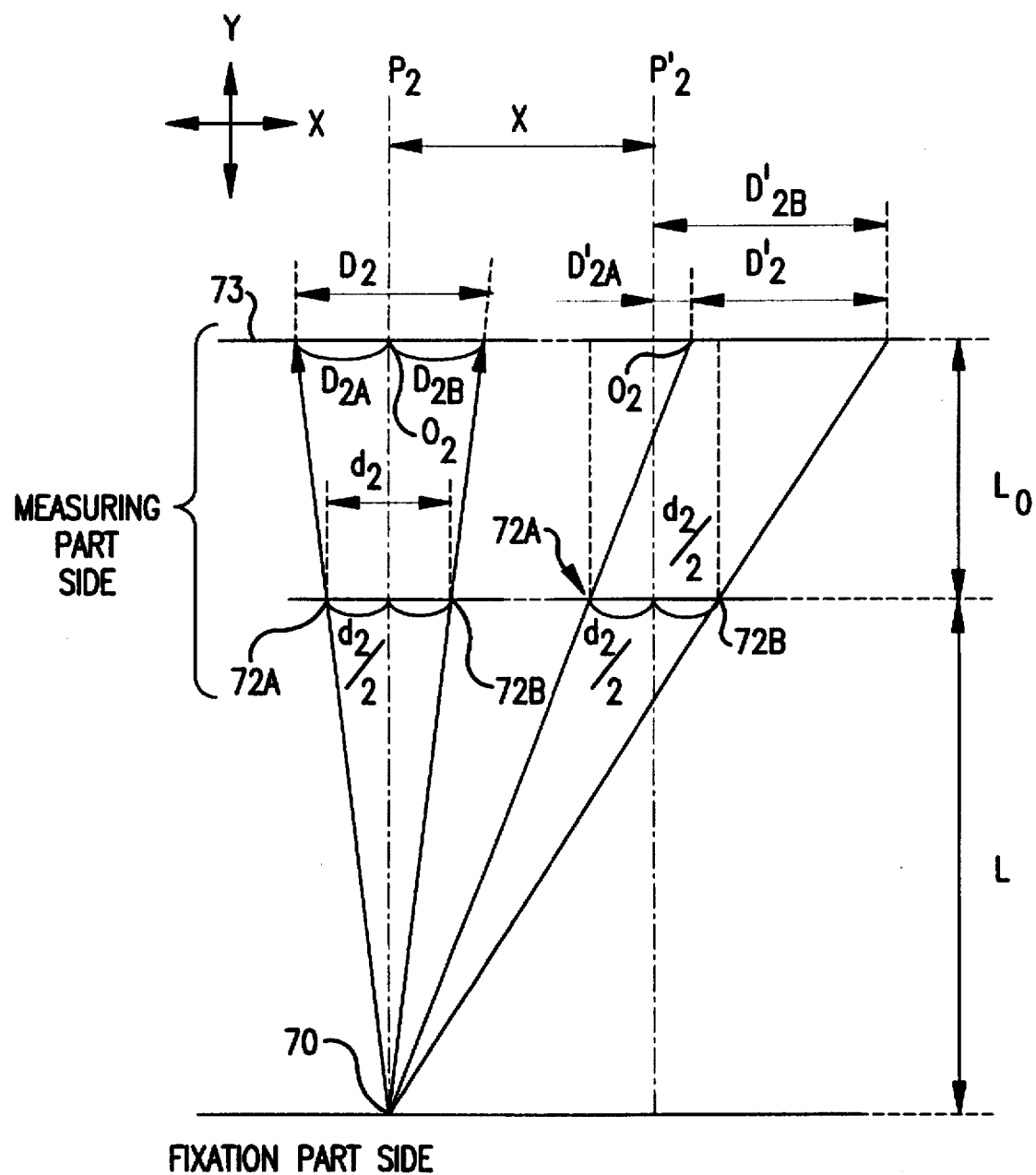
FIG. 8 is a view for illustrating a method for detecting a relative position in a right and left direction of a measuring part of a construction of a second preferred embodiment; and, FIG. 9 is a view showing a mechanism for detecting a moving distance for obtaining a moving distance of an inspecting-measuring part of an apparatus manufactured by using a prior art.
Figure 9:
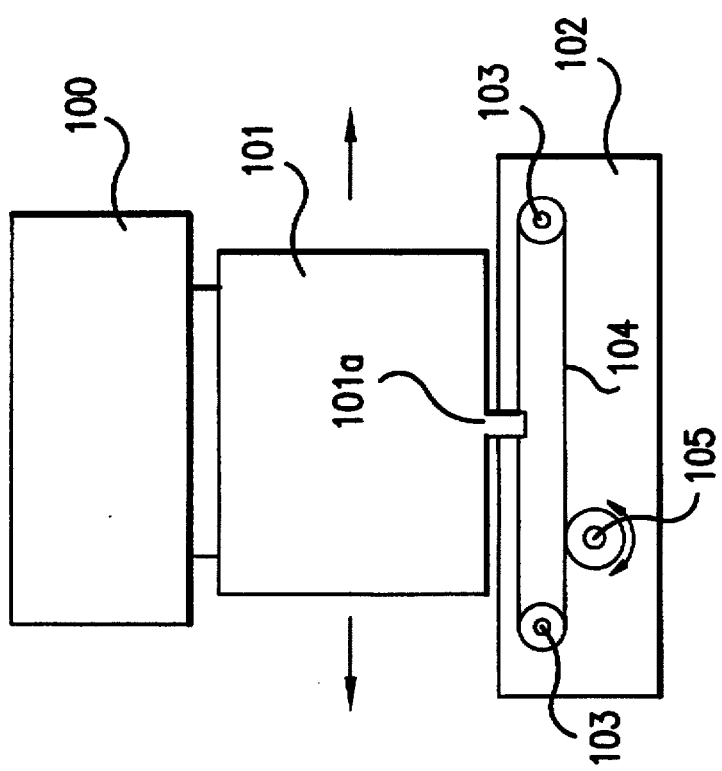

A method for detecting according to construction of the second preferred embodiment will be described referring to FIG. 8.

First of all, as the same as the first preferred embodiment, it is considered about a detection of a distance of the measuring part 5 in a Y-direction from the fixation stand 1 (it is considered concerning a X-Y plane, under the condition that a before and behind (Z) direction is defined as constant). Here, a perpendicular plane against a light source 70 disposed on a fixation stand 1 is defined as a standard position $P_2$ in a right and left direction, and the middle of two pieces of slit apertures 72A and 72B that are placed at interval of an interval $d_2$ against a standard position $P_2$ in a right and left direction and a standard point $O_2$ on an one-dimensional photo detecting element 73 are defined as to be at a position $P'_2$ where is a distance x apart from a standard position $P_2$ in a right and left direction. Additionally, in a height direction (Y-direction), slit apertures 72A and 72B are defined as to be at a distance L apart from the light source 70 in a vertical direction. A distance from the slit aperture 72 to a detecting plane of the one-dimensional photo detecting element 73 is a fixed distance, it is defined as $L_o$. At this time, if an interval of slit images between the slit apertures 72A and 72B that are caused by the light source 70 is defined as $D'_2$, there is a relationship given by the following expression (concerning an interval $D_2$ of slit images at a standard position $P_2$ in a right and left position, it is the same):

$$D'_2 : d_2 = (L+L_o) : L \tag{8}$$

Where a distance L is given by the following expression referring to this relationship:

$$L = (L_o * d_2)/(D'_2 - d_2) \tag{9}$$

Where $L_o$ and $d_2$ are decided under a design, and $D'_2$ is obtained on the basis of a detection by the one-dimensional photo detecting element 73, therefore a distance L can be decided.

Next, if a distance L can be decided, as the same as the first preferred embodiment, a moving distance x of a position $P'_2$ in a right and left direction against a standard position $P_2$ in a right and left direction is obtained on the basis of a displacement against a standard point $O_2$ of either slit images. For example, in the case of a position $P'_2$, if a displacement from a standard point $O_2$ of a slit image caused by the slit aperture 72B is defined as $D'_{2B}$ (in the figure, a right direction against a standard point $O_2$ is defined as "+"), there is a relationship given by the following expression:

$$(x+d_2/2):(D'_{2B}-d_2/2)=L:L_o \tag{10}$$

Where x is given by following expression:

$$x=(L/L_o) * (D'_2B-d_2/2)-(d_2/2) \tag{11}$$

Then following expression is given by substituting L of the expression (8) for the expression (11):

$$x=[d_2 * (D'_2B-d_2/2)/(D'_2-d_2)]-(d_2/2) \tag{12}$$

Additionally, in consideration of a slit image caused by the slit aperture 72A, if a displacement of a slit image from a standard point $O_2$ is defined as $D'_{2A}$, the following expression is given:

$$x=[d_2 * (D'_{2A}+d_2/2)/(D'_2-d_2)]+(d_2/2) \tag{13}$$

Where $d_2$ is known in advance since it is decided under a design, and a displacement $D'_{2B}$ ($D'_{2A}$) of a slit image from a standard point $O_2$ caused by the slit aperture 72B (or the slit aperture 72A) and an interval $D'_2$ between two slits are values detected by the one-dimensional photo detecting element 73. Therefore, if movements by the two slit images are detected on the one-dimensional photo detecting element 73, a moving quantity of the measuring part 5 in a right and left direction against the fixation stand 1 can be obtained according to calculation based on above-expressions (expressions (11) or (12)).

Additionally, whether it moves to a right direction or a left direction against a standard position $P_2$ in a right and left direction can be known on the basis of a position of a middle point between two slits against a standard point $O_2$.

The present invention may be embodied in other specific forms without departing from the spirit or essential characteristics thereof. For instance, in the second preferred embodiment, two pieces of slit apertures are used against one piece of light source, however it may be considered that a number of slit apertures is greater than that. Further, a number of a light source and a number of a slit aperture can be respectively made to be the plural number by combining the first preferred embodiment with the second preferred embodiment.

The forgoing description of the preferred embodiments of the invention has been presented for purposes of illustration and descripton. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalates.

What is claimed is:

1. An ophthalmic apparatus in which a measuring part for inspecting-or-measuring an eye to be examined is disposed so as to move relatively against a fixation stand, the ophthalmic apparatus comprising:

light source for use in detecting a relative movement, which is disposed in the one between said fixation stand side and said measuring part side;

photo detecting elements for detecting a light bundle emitted from said light source for use in detecting a relative movement, which is disposed in the other between said fixation stand side and said measuring part side;

target forming means for forming at least two target-images, that are transmitted from said light source for use in detecting a relative movement onto said photo detecting elements plane, upon before and after the movement according to the relative movement by said measuring means against the fixation stand; and calculating means for calculating a relative position of said measuring part against said fixation stand based on a detecting information of said target images detected by said photo detecting elements.

2. An ophthalmic apparatus according to claim 1, wherein plural number of said light sources for use in detecting a relative movement are disposed in a direction for detecting a relative position between said measuring part and said fixation stand at intervals of a predetermined distance, and a target plate having one slit-aperture for limiting an incidence of a light bundle is disposed in an optical system of which the light bundle emitted from said light source is detected by said photo detecting element.

3. An ophthalmic apparatus according to claim 2, wherein said target plate has an arc plane, and said photo detecting element is an one-dimensional detecting element disposed at an approximate center of curvature.

4. An ophthalmic apparatus according to claim 2, further comprising:

examined-eye fixating means for fixating an examined-eye against said fixation stand; and judging means for judging whether the examined-eye fixed by said examined-eye fixating means is right side or left side based on a detected-information for a target image detected by said photo detecting element.

5. An ophthalmic apparatus according to claim 1, a target plate having two slit-apertures for limiting an incidence of a light bundle emitted from said light source is disposed in an optical system of which the light bundle emitted from said light source for use in detecting a relative movement is detected by said photo detecting element.

6. An ophthalmic apparatus according to claim 5, further comprising:

examined-eye fixating means for fixating an examined-eye against said fixation stand; and judging means for judging whether the examined-eye fixed by said examined-eye fixating means is right side or left side based on a detected-information for a target image detected by said photo detecting element.

7. An ophthalmic apparatus according to claim 1, wherein said calculating means calculates a moving-quantity for a relative position in a right-and-left direction of said measuring part against said fixation stand.

8. An ophthalmic apparatus according to claim 7, further comprising interpupilary distance measuring means for measuring a interpupilary distance of an examinee based on an information for the relative position in a right-and-left direction of said measuring part, which is calculated by said calculating means.

9. An ophthalmic apparatus according to claim 1, further comprising:

vertical position detecting means for detecting a position in a vertical direction of said measuring part against said fixation stand; and calculating means for calculating a relative position in a before-and-behind direction of said measuring part against said fixation stand based on a detecting information detected by said vertical position detecting means and said photo detecting elements.

10. An ophthalmic apparatus in which a measuring part for inspecting-or-measuring an eye to be examined is disposed so as to move relatively against a fixation stand, the ophthalmic apparatus comprising:

movable part for moving relatively against a fixation stand by an examinee's operation;

measuring-part-moving-means for moving further a measuring part relatively against said movable part;

light source for use in detecting a relative movement, which is disposed in the one between said fixation stand side and said measuring part side;

photo detecting elements for detecting a light bundle emitted from said light source for use in detecting a relative movement, which is disposed in the other between said fixation stand side and said measuring part side;

target forming means for forming at least two target-images, that are transmitted from said light source for use in detecting a relative movement onto said photo detecting elements plane, upon before and after the movement according to the relative movement by said measuring means against the fixation stand; and calculating means for calculating a relative position of said measuring part against said fixation stand based on a detecting information of said target images detected by said photo detecting elements.

11. An ophthalmic apparatus according to claim 10, wherein plural number of said light sources for use in detecting a relative movement are disposed in a direction for detecting a relative position between said measuring part and said fixation stand at intervals of a predetermined distance, and a target plate having one slit-aperture for limiting an incidence of a light bundle is disposed in an optical system of which the light bundle emitted from said light source is detected by said photo detecting element.

12. An ophthalmic apparatus according to claim 11, wherein said target plate has an arc plane, and said photo detecting element is an one-dimensional detecting element disposed at an approximate center of curvature.

13. An ophthalmic apparatus according to claim 10, a target plate having two slit-apertures for limiting an incidence of a light bundle emitted from said light source is disposed in an optical system of which the light bundle emitted from said light source for use in detecting a relative movement is detected by said photo detecting element.

14. An ophthalmic apparatus according to claim 10, wherein calculating means for calculating a moving-quantity for a relative position in a right-and-left direction of said measuring part against said fixation stand.

15. An ophthalmic apparatus according to claim 14, further comprising interpupilary distance measuring means for measuring a interpupilary distance of an examinee based on an information for the relative position in a right-and-left direction of said measuring part, which is calculated by said calculating means.

16. An ophthalmic apparatus according to claim 10, further comprising:

alignment detecting means for detecting an aligning condition between a measuring system contained in said measuring part and the examined-eye; and control means for driving said means for moving a measuring part based on a result detected by said alignment detecting means.

17. An ophthalmic apparatus in which a measuring part for inspecting-or-measuring an eye to be examined is disposed so as to move relatively against a fixation stand, the ophthalmic apparatus comprising:

light source for use in detecting a relative movement, which is disposed in the one between said fixation stand side and said measuring part side;

photo detecting elements for detecting a light bundle emitted from said light source for use in detecting a relative movement, which is disposed in the other between said fixation stand side and said measuring part side;

target forming means for forming at least two target-images, that are transmitted from said light source for use in detecting a relative movement onto said photo detecting elements plane, upon before and after the movement according to the relative movement by said measuring means against the fixation stand;

vertical position detecting means for detecting a position in a vertical direction of said measuring part against said fixation stand; and calculating means for calculating a relative position in a before-and-behind direction of said measuring part against said fixation stand based on a detecting information detected by said vertical position detecting means and said photo detecting elements.

* * * * *